US00PP26720P3

(12) United States Plant Patent

Klemm et al.

(10) Patent No.: US PP26,720 P3

(45) Date of Patent: May 10, 2016

(54) *DIANTHUS* PLANT NAMED 'KLEDP14205'

(50) Latin Name: *Dianthus caryophyllus*
Varietal Denomination: KLEDP14205

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 109 days.

(21) Appl. No.: 14/120,254

(22) Filed: May 13, 2014

(65) Prior Publication Data

US 2015/0334895 P1 Nov. 19, 2015

(51) Int. Cl.
*A01H 5/02* (2006.01)

(52) U.S. Cl.
USPC ..... Plt./278

(58) Field of Classification Search
USPC ..... Plt./273, 278
See application file for complete search history.

*Primary Examiner* — Susan McCormick Ewoldt
(74) *Attorney, Agent, or Firm* — Barbara Campbell; Bethany R. Roahrig; Cochran Freund & Young, LLC

(57) ABSTRACT

A new *Dianthus* plant particularly distinguished by red flowers with white margins and an upright form, is disclosed.

1 Drawing Sheet

Genus and species: *Dianthus caryophyllus*.
Variety denomination: 'KLEDP14205'.

BACKGROUND OF THE NEW PLANT

The present invention comprises a new and distinct variety of *Dianthus*, botanically known as *Dianthus caryophyllus*, and hereinafter referred to by the variety name 'KLEDP14205'. 'KLEDP14205' originated from a branch mutation of the proprietary mutation parent 'DCP 2010-1006' (unpatented) in May 2010 in in a greenhouse in Italy.

In June 2010, 'KLEDP14205' was first vegetatively propagated by vegetative cuttings. 'KLEDP14205' was found to reproduce true to type in successive generations of asexual propagation in Stuttgart, Germany via vegetative cuttings.

SUMMARY

The following are the most outstanding and distinguishing characteristics of this new variety when grown under normal horticultural practices in Stuttgart, Germany.

1. Red flowers with white margins; and
2. An upright form.

DESCRIPTION OF THE PHOTOGRAPH

This new *Dianthus* plant is illustrated by the accompanying photograph of a plant approximately 5-months old and grown in a glass greenhouse in Stuttgart, Germany. The photograph shows the whole plant, including the flowers and foliage and buds and was taken in May 2012 in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEDP14205'. The data which define these characteristics were collected from asexual reproductions carried out in Stuttgart, Germany. Data was collected on 5-month old plants grown in a greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP14205'.

Parentage:
- *Mutation parent*.—The proprietary *Dianthus* variety 'DCP 2010-1006' (unpatented).

Plant:
- *Propagation type*.—Vegetative cuttings.
- *Time to produce a rooted young plant*.—14 to 16 days.
- *Root description*.—White, fine.
- *Rooting habit*.—Lanceolate.
- *Plant form*.—Potted plant, upright.
- *Plant height*.—13.0 cm to 15.0 cm.
- *Plant diameter or spread*.—20.0 cm to 22.0 cm.

Lateral branches:
- *Length*.—8.0 cm to 10.0 cm.
- *Diameter*.—3.0 mm to 5.0 mm.
- *Internode length*.—0.6 cm to 0.8 cm.
- *Number of internodes per branch/stem*.—4.
- *Node length*.—0.3 cm to 0.4 cm.
- *Node diameter*.—0.3 cm.
- *Texture*.—Smooth.
- *Color*.—RHS N137B.
- *Branch/stem*.—Solid.

Foliage:
- *Arrangement*.—Opposite.
- *Length*.—4.0 cm to 6.0 cm.
- *Width*.—0.6 cm to 0.8 cm.
- *Shape*.—Lanceolate.
- *Apex*.—Acute.
- *Base*.—Obtuse.
- *Margin*.—Entire.
- *Texture* (*both upper and lower surfaces*).—Smooth.

*Immature leaf color* (*both upper and lower surfaces*).—RHS 143A.

*Mature leaf color*.—Upper surface: RHS N137C. Lower surface: RHS N137D.

*Venation pattern*.—Parallel.

*Venation color* (*both upper and lower surfaces*).—RHS N137.

Flowers:

*Flower type and habit*.—Double, round, and small sprays.

*Fragrance*.—Present.

*Natural flowering season*.—Spring to fall.

*Position of flowers relative to the foliage*.—Slightly above.

*Number of flowers per spray*.—3 to 5.

*Flower longevity*.—10 to 12 days.

*Buds*.—Length: 1.7 cm to 2.0 cm. Diameter: 0.8 cm to 1.0 cm. Shape: Elliptic. Color: RHS 137B and RHS 143C. Extrusion of the styles at the bud stage: No.

*Corolla*.—Quantity of petals and arrangement: 15 to 20 petals arranged in several whorls. Corolla height: 1.5 cm to 2.0 cm. Petal length: 3.5 cm. Petal width: 1.4 cm to 1.8 cm. Petal shape: Spoon-shaped. Petal apex: Obtuse. Petal base: Acute. Petal margin: Crenate and medium deep. Petal texture (both upper and lower surfaces): Smooth. Petal color: Immature: Upper surface: RHS 50A and RHS N155B on the margins. Lower surface: RHS 54D. Mature: Upper surface: RHS 50B and N155B on the margins. Lower surface: RHS 49D.

*Calyx*.—Quantity of sepals and arrangement: Composed of 4 to 5 fused sepals. Shape: Campanulate. Calyx height: 1.8 cm to 2.0 cm. Calyx diameter (at the apex): 0.8 cm to 1.0 cm. Sepal texture (both upper and lower surfaces): Smooth. Sepal color: Upper surface: RHS N137B. Lower surface: RHS 137C.

Peduncles:

*Length*.—10.0 cm to 14.0 cm.

*Diameter*.—0.2 cm.

*Strength*.—Moderate.

*Texture*.—Smooth.

*Color*.—RHS 137A.

Reproductive organs:

*Stamens*.—Quantity per flower: 3 to 5. Filament length: 0.5 cm to 0.7 cm. Filament color: RHS 155B. Anther length: 0.1 cm. Anther diameter: 0.05 cm. Anther color: RHS 19B. Pollen amount: Sparse.

*Pistils*.—Quantity per flower: 1. Pistil length: 0.1 cm. Style length: 1.6 cm to 1.8 cm. Style color: RHS 59A. Stigma shape: Filamentous. Stigma color: RHS 59A. Ovary size: 0.4 cm to 0.6 cm. Ovary shape: Oval. Ovary color: RHS 145A.

Fruit and seed set: Seed sometimes observed; additional information on seed not available.

Disease and pest/insect resistance: No disease and pest/insect resistance observed.

COMPARISON WITH PARENTAL LINE AND KNOWN VARIETY

'KLEDP14205' is a distinct variety of *Dianthus* and is distinguished from the mutation parent as described in Table 1.

TABLE 1

Comparison with Parental Lines

| Characteristic | 'KLEDP14205' | Mutation Parent 'DCP 2010-1006' |
|---|---|---|
| Flower color | Red with white margins | Red |

'KLEDP14205' is a distinct variety of *Dianthus* and is most similar to the commercial *Dianthus* variety 'KLEDP10105' (U.S. Plant Pat. No. 23,133), also commercially known as SuperTrouper™ 'Oscar'. Differences between the varieties are described in Table 2.

TABLE 2

Comparison with Similar Variety

| Characteristic | 'KLEDP14205' | 'KLEDP10105' |
|---|---|---|
| Flower color | Red with white margins | Dark pink with purple eyes |

We claim:

1. A new and distinct variety of *Dianthus* plant designated 'KLEDP14205' as illustrated and described herein.

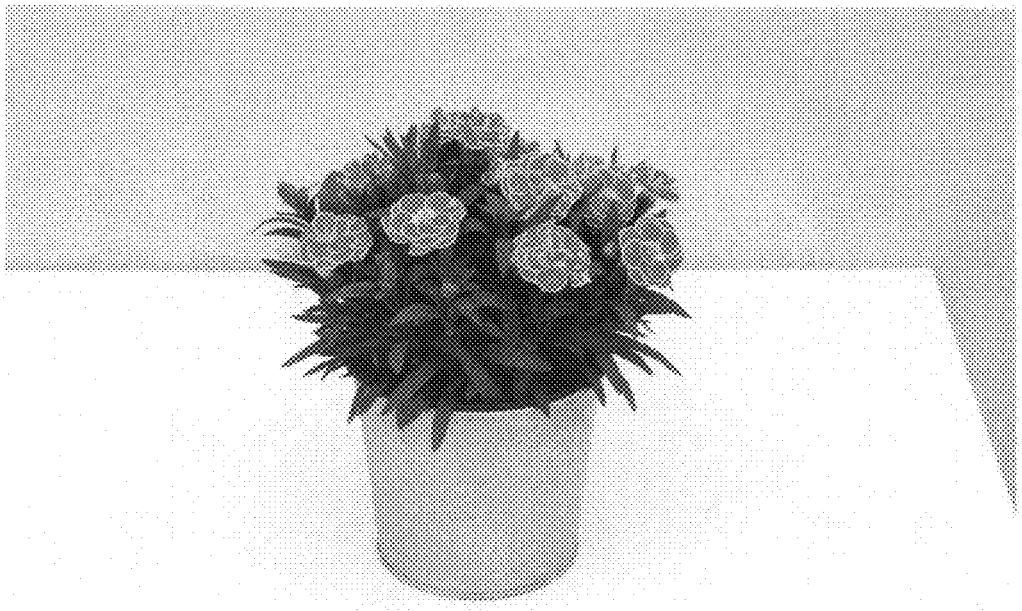

* * * * *